United States Patent [19]

MacKay et al.

[11] Patent Number: 5,824,842
[45] Date of Patent: Oct. 20, 1998

[54] METHOD OF ALTERING LIGNIN IN TREES

[75] Inventors: John MacKay, Raleigh; David O'Malley, Cary; Ross Whetten; Ronald Sederoff, both of Raleigh, all of N.C.

[73] Assignee: North Carolina State University, Raleigh, N.C.

[21] Appl. No.: 687,646

[22] Filed: Jul. 26, 1996

[51] Int. Cl.$^6$ .............................. A01G 1/00; A01H 1/04; A01H 1/00; A01H 3/00
[52] U.S. Cl. .................. 800/200; 800/205; 800/230; 800/DIG. 51; 800/DIG. 49; 536/23.6; 47/58
[58] Field of Search ................................. 800/200, 205, 800/DIG. 51, DIG. 49, 230; 47/58; 536/23.6

[56] References Cited

U.S. PATENT DOCUMENTS

| | | | |
|---|---|---|---|
| 4,687,741 | 8/1987 | Farrell et al. | 435/189 |
| 5,122,466 | 6/1992 | Stomp et al. | 435/172.3 |
| 5,451,514 | 9/1995 | Boudet et al. | 435/172.3 |

FOREIGN PATENT DOCUMENTS

| | | |
|---|---|---|
| WO93/24638 | 12/1993 | WIPO . |
| WO95/27790 | 10/1995 | WIPO . |

OTHER PUBLICATIONS

King and Stansfield. Dictionary of Genetics. Oxford University Press, 1985, p. 269.

J. J. MacKay et al.; genetic analysis of cinnamyl alchohol dehydrogenase in loblolly pine: single gene inheritance, molecular characterization and evolution, *Mol. Gen. Genet.* 247:537–545 (1995).

C. Halpin et al.; Manipulation of lignin quality by down-regulation of cinnamyl alcohol dehydrogenase, *The Plant Journal* 6(3):339–350 (1994).

*Primary Examiner*—David T. Fox
*Assistant Examiner*—Thomas Haas
*Attorney, Agent, or Firm*—Myers Bigel Sibley & Sajovec, L.L.P.

[57] ABSTRACT

Methods of providing and breeding trees having more easily extractable lignin due to the presence of a cinnamyl alcohol dehydrogenase (Cad) null gene are presented.

19 Claims, 12 Drawing Sheets

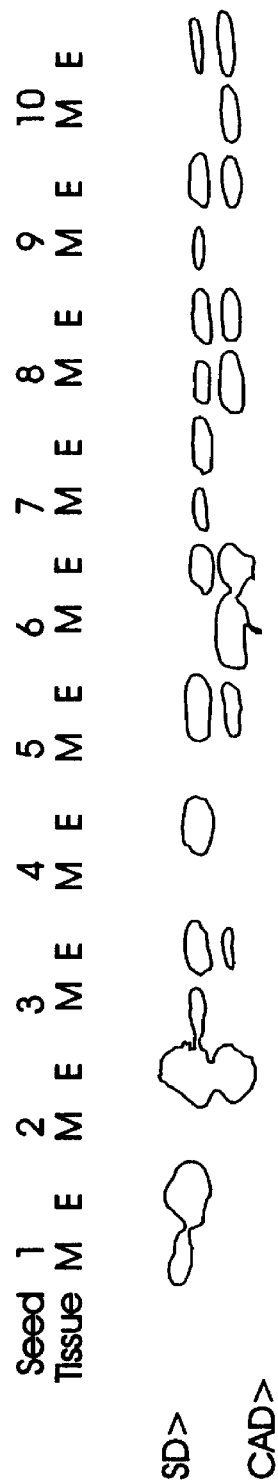
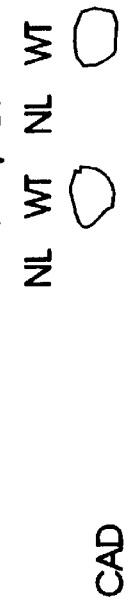
FIG. 2B
FIG. 4A
FIG. 4B

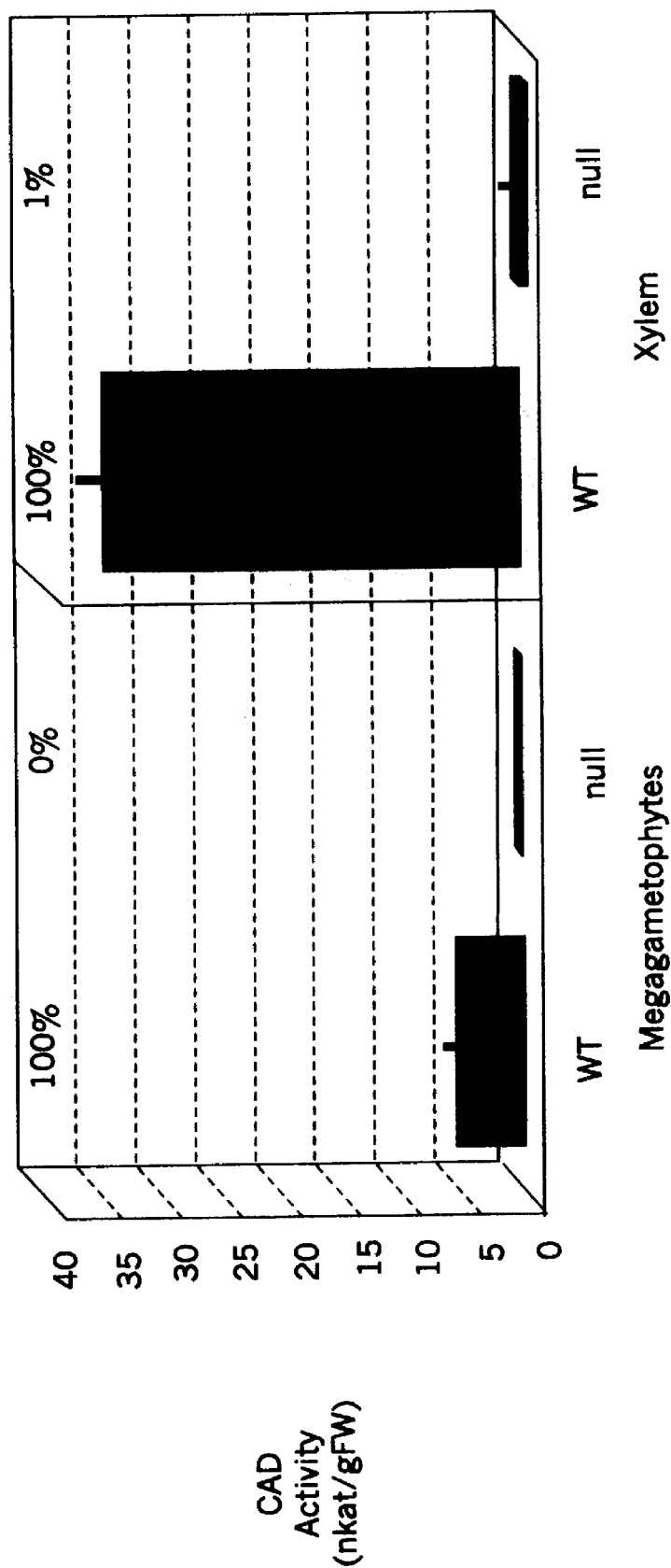

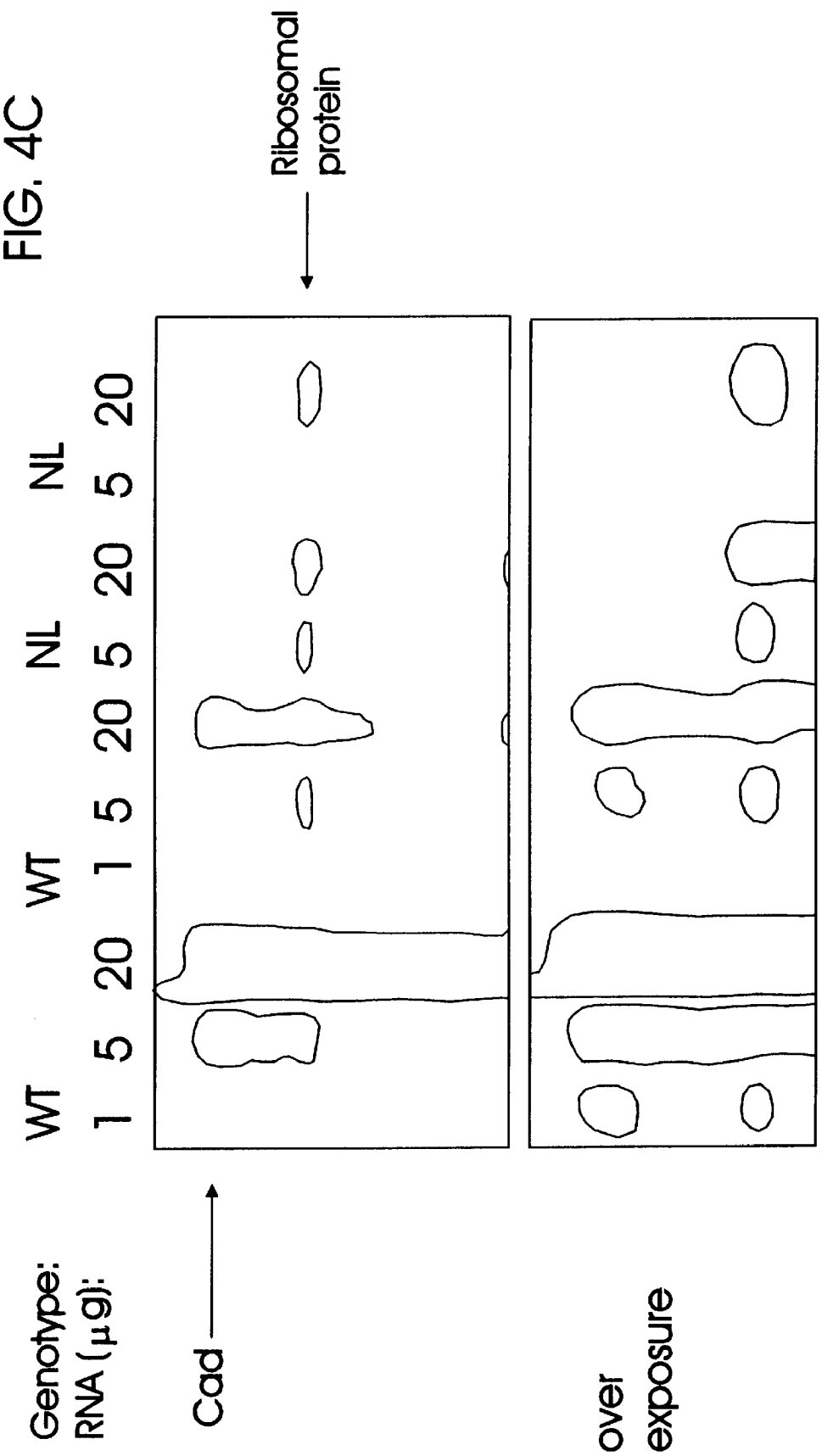

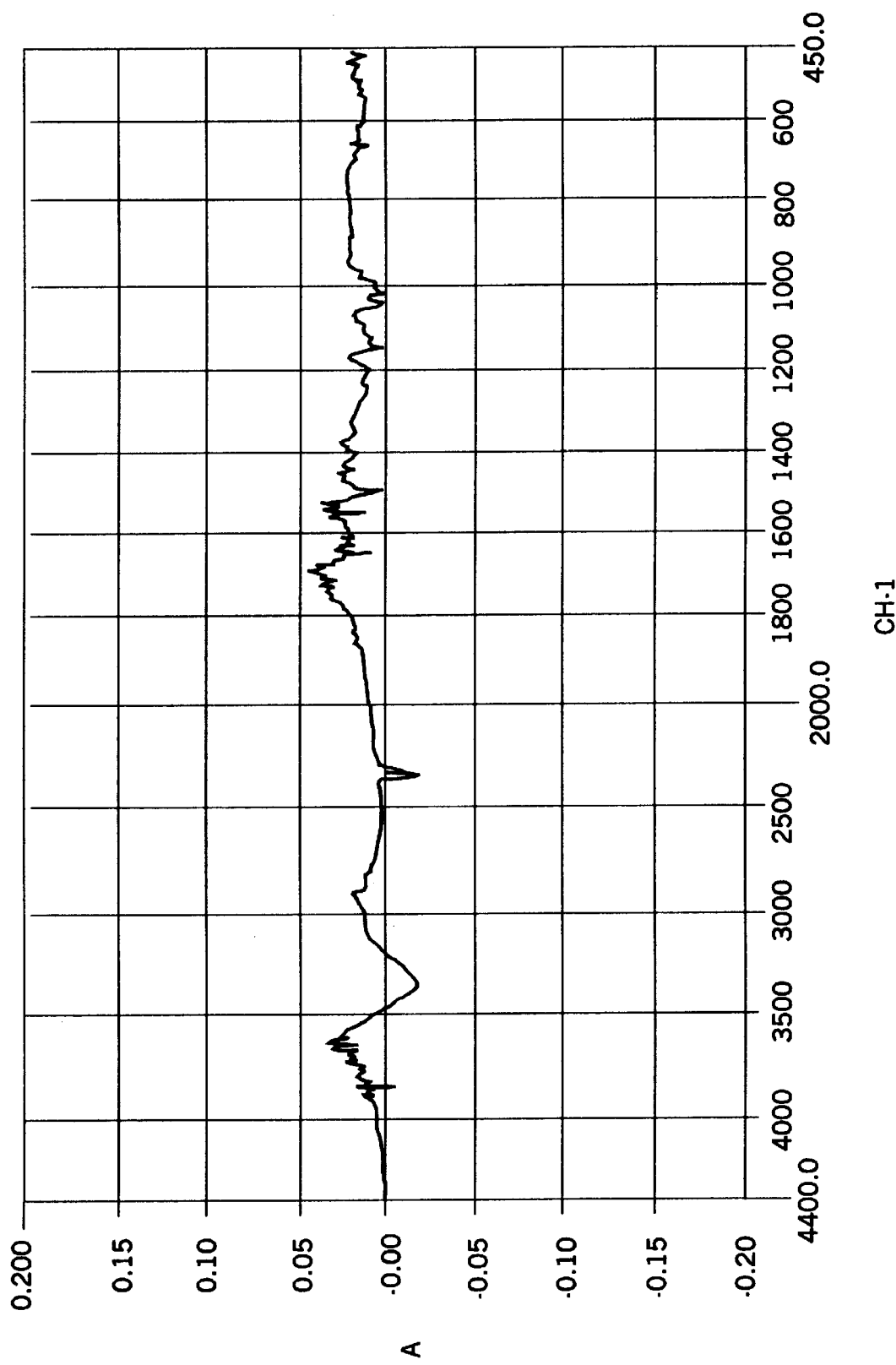

METHOD OF ALTERING LIGNIN IN TREES

This invention was made with government support under Grant No. DE-FG05-92ER20085 awarded by the U.S. Department of Energy and Grant No. 91-37304-6581 awarded by the U.S. Department of Agriculture. The government has certain rights in this invention.

FIELD OF THE INVENTION

The present invention relates to methods of providing and breeding trees having more easily extractable lignin due to the presence of a cinnamyl alcohol dehydrogenase (Cad) null gene.

BACKGROUND OF THE INVENTION

Up to thirty-six percent of the dry weight of wood is lignin; during pulp and papermaking lignin must be separated from cellulose. This process consumes large amounts of energy and imposes a high environmental cost due to the requirement for chemicals such as chlorine bleach. The availability of wood with a reduced lignin content or with modified lignin which is more amenable to extraction would increase the efficiency of pulp and papermaking processes and decrease chemical consumption.

In crop plants, increased lignin content decreases the digestibility and energy value of forage plants. Mutant lines of grasses (maize, sorghum and pearl millet) are known that have a reduced lignin content and improved digestibility. Cherney et al., *Adv. Agron.* 46:157–198 (1991). These plants have a distinctive phenotype with brown-red xylem tissues and are known as "brown-midrib" mutants; they have reduced lignin content and in some cases modified lignin composition. Kuc et al. *Phytochemistry* 7:1435 (1968); Muller et al. *Crop Sci.* 11:413 (1971). Brown-midrib has been reported to result from mutations at a number of different steps in the lignin biosynthetic pathway, including mutations in cinnamyl alcohol dehydrogenase (CAD) in sorghum bm6 (Pillonel *J.Planta* 185:538 (1991)). No complete loss-of-function mutations have yet been identified in brown-midrib mutants.

Lignin is a complex heterogenous aromatic polymer found in the cell walls of higher plants. It is formed by oxidative polymerization involving three different lignin precursor alcohols (p-hydroxycinnamyl alcohol, coniferyl and sinapyl alcohol) collectively referred to as monolignols, and involves enzymatic functions that are not completely characterized. Lignins from different plants, and from different tissues within a plant, may vary in monolignol composition or the relative content of different monolignols, possibly due to different activities and substrate specificities of lignin biosynthetic enzymes from different sources. Higuchi, In: *Biosynthesis and Degradation of Wood Components* (Higuchi, Ed.), Orlando: Academic Press, pp. 141–160.

All lignins may be characterized by the relative proportions of the three major phenyl propanoid units (guaiacyl units, derived from coniferyl alcohol (G units); syringyl units derived from sinapyl alcohol (S units); and p-hydroxyphenyl units (H units) derived from p-coumaryl alcohol). A typical conifer lignin contains predominantly guaiacyl units, with only a trace of S units. A woody angiosperm such as poplar or oak contains roughly equivalent amounts of G and S units. Many higher plants have the capacity to synthesize the three major types of lignin subunits, but the different types of lignin can result from developmental and environmental regulation of gene expression or metabolic flux. See, e.g., Chiang et al., *Tappi J.* 71:173–176 (1988); Sarkanen and Hergert, *In Lignins: Occurrence, Formation, Structure and Reactions* (Sarkanen and Ludwig, eds.) N.Y.: Wiley-Interscience, pp. 43–94 (1971).

Lignin is a product of the phenylpropanoid pathway, and several genes have been isolated which encode enzymes specific to monolignol biosynthesis. Two enzymes are known which function after branch points leading to the monolignol biosynthetic pathway: cinnamoyl-CoA reductase (CCR) and cinnamyl alcohol dehydrogenase (CAD; E.C. 1.1.1.195). CAD catalyzes the conversion of cinnamaldehyde to cinnamyl alcohols, the final step in the biosynthesis of monolignols. Cad expression begins in the early stages of xylogenesis, before lignin deposition (O'Malley et al., *Plant Physiol* 98:1364 1992). CAD can be expressed in cells which are not involved in lignin synthesis as well as those actively making lignin. Cad genes have been cloned from several species, including tobacco (*Nicotiana tabacum;* Knight et al., *Plant Mol. Biol.* 19:793 (1992)), eucalypt (*Eucalyptus gunii;* Grima-Pettenati et al. *Plant Mol. Biol.* 21:1085 (1993)), aralia (*Aralia cordata;* Hibino et al. *Plant Cell. Physiol.* 34:659 (1993)), hybrid poplar and alfalfa (*Populus deltoides* X *Populus trichocarpa* and *Medicago sativa;* Van Doorsselaere et al. *Plant Physiol. Biochem.* 33:105 (1995)), spruce (*Picea abies;* Galliano et al., *Plant Mol. Biol.* 23:145 (1993)) and pine (*Pinus taeda,* O'Malley et al., *Plant Physiol* 98:1364 (1992)).

SUMMARY OF THE INVENTION

A first aspect of the present invention is a method of producing a stand of conifer trees with each individual tree within the stand having easily extractable lignin. In the method, a sexually mature conifer tree homozygous for a Cad null allele is crossed with another tree of the same species; the resulting seeds are collected and germinated to produce a number of $F_1$ progeny trees which are heterozygous or homozygous for the Cad null allele, which are planted in a stand. Each tree contains lignin which is more easily extractable compared to lignin in a wild-type tree of the same species.

A further aspect of the present invention is a method of producing a stand of clonal conifer trees having easily extractable lignin. The method involves crossing a conifer tree homozygous or heterozygous for a Cad null allele with another tree of the same species to produce a plurality of seeds, germinating the seeds to produce $F_1$ progeny trees, and assessing the progeny for the presence of the Cad null allele. A single tree containing the Cad null allele is selected and cloned, and a stand of the clonal trees is produced. Each tree within the stand contains lignin which is more easily extractable compared to lignin in a wild-type tree of the same species.

A further aspect is a method of producing a stand of conifer trees having easily extractable lignin, wherein two conifer trees heterozygous for a Cad null allele are crossed, and the $F_1$ progeny are assessed for the Cad null allele. Progeny which contain a Cad null allele are selected and propagated in a stand; each tree within the stand contains lignin which is more easily extractable compared to lignin in a wild-type tree of the same species.

A further aspect of the present invention is a stand of conifer trees homozygous for a Cad null allele and containing lignin which is more easily extracted compared to wild-type trees of the same species.

A further aspect of the present invention is a stand of clonal homozygous Cad null loblolly pine trees.

BRIEF DESCRIPTION OF THE DRAWINGS

FIG. 2B is a native PAGE analysis of CAD null inheritance in ten selfed progeny of loblolly pine clone 7-56. 'M' indicates megagametophyte tissue and 'E' indicates embryo tissue extracts; extracts of the same seed were run side-by-side and stained for CAD activity and for shikimate dehydrogenase (SD) as a control.

FIG. 3A is a graph comparing the CAD enzyme activity in protein extracts of wild-type (WT) and Cad null (null) haploid megagametophyte tissue and diploid xylem tissue.

FIG. 4A is a Northern blot probed with the Cad gene using shoot tip tissue from Cad null (NL) or wild-type (WT) loblolly pine plants, 10 μg of total RNA per lane, indicating that the level of steady state Cad RNA message (CAD) in null tissue was lower than the threshold of detection (top panel); the blot was stripped and reprobed with a gene encoding a pine ribosomal protein (Rb prot.) as a positive control (lower panel).

FIG. 4B is a Northern blot using megagametophyte tissue from Cad null (NL) or wild-type (WT) loblolly pine plants, 4 μg of total RNA per lane, indicating that the level of steady state Cad RNA message (CAD) in null tissue was lower than the threshold of detection (top panel); the blot was stripped and reprobed with a gene encoding a pine ribosomal protein (Rb prot.) as a positive control (lower panel).

FIG. 4C depicts the results of RNAse protection assays using RNA obtained from the xylem of wild-type (WT) or Cad null (NL) loblolly pine trees, where Cad indicated steady-state RNA message of Cad compared to that of ribosomal protein. Each wild-type sample was run at 1 μg, 5 μg, and 20 μg of tissue; each null sample was run at 5 μg and 20 μg of tissue. The bottom panel of FIG. 4C is an over-exposure of the same film, giving the same comparative results.

FIG. 6C graphs an infrared subtraction spectrum obtained by subtracting the spectrum from a wild-type loblolly pine plant from a second spectrum of a wild-type loblolly pine plant. "A" indicates carbonyl groups conjugated to aromatic rings, "B" indicates lignin.

DETAILED DESCRIPTION OF THE INVENTION

Figure 1:
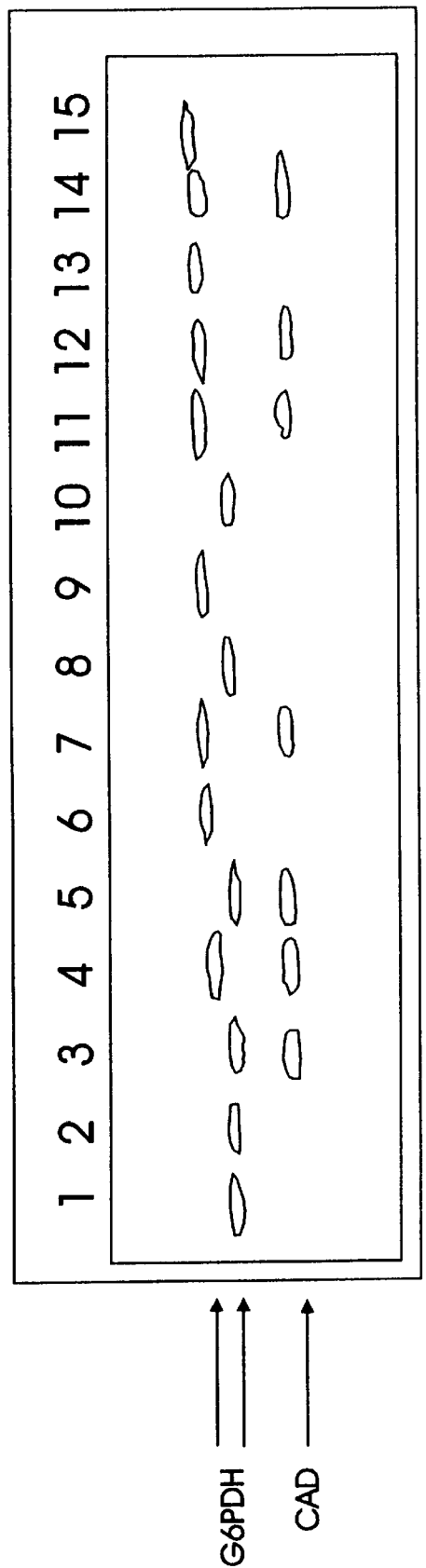
FIG. 1 is a gel in which crude megagametophyte protein extracts obtained from fifteen loblolly pine clone 7-56 seeds (open-pollinated) were separated by non-denaturing PAGE, and stained to reveal both CAD and glucose-6-phosphate dehydrogenase (G6PDH).

The present inventors have discovered a naturally occurring mutation in loblolly pine that blocks cinnamyl alcohol dehydrogenase (CAD), a key enzyme in the lignin biosynthetic pathway. The mutation maps to the same location in the genome (on a genetic map) as the structural gene encoding the enzyme. The mutation blocks the reduction of cinnamyl aldehydes to cinnamyl alcohols, the major precursors of lignin. Results indicate that coniferaldehyde is polymerized into lignin in Cad null mutants, resulting in wood that is different in lignin content and/or composition. In pine the mutation has been found to be stable over generations, not tissue specific, uniform in phenotypic effect, and to reduce expression of CAD to 1% or less of normal activity.

Halpin et al. describe the reduction of CAD activity and alteration of lignin composition in transgenic tobacco plants using antisense RNA. Reduction of CAD activity to 7% of wild type did not affect the quantity of lignin in the CAD antisense plants, but the lignin contained an increased proportion of cinnamyl aldehydes to cinnamyl alcohols. This lignin was more accessible to chemical extraction. The plants also had vascular tissue with a brown-red coloration. Halpin et al., *The Plant Journal* 6:339 (1994). Similar observations have been made with antisense CAD in poplar (Baucher et al., *IUFRO Molecular Genetics Workshop*, Prouts neck, Me., (May 1994); Hibino et al., *Biosci. Biotech. Biochem.* 59:929–31 (1994).

A method of inhibiting lignin biosynthesis is described in U.S. Pat. No. 5,451,514 to Boudet et al., comprising stably transforming plant cells with a DNA construct encoding an mRNA which is substantially homologous or complementary to mRNA encoded by the endogenous Cad gene. Transcribed mRNA acts to inhibit production of the enzyme by the endogenous gene. To decrease CAD production, the inserted DNA (a Cad gene or portion thereof) may be in an antisense orientation.

In plants, the gene encoding the enzyme cinnamyl alcohol dehydrogenase (CAD) is expressed in response to different developmental and environmental cues. While few plant cell types normally accumulate lignin, lignin deposition can be induced by disease or wounding in many cell types. In loblolly pine (*Pinus taeda L.*) several electrophoretic variants (allozymes) of CAD, and a high level of heterozygosity ($h_e$=0.46), have been found. MacKay et al., *Mol. Gen. Genet.* 247:537 (1995). The CAD enzyme in loblolly pine has been found to be encoded by one Cad gene (with several allelic variants), and to be expressed in both lignifying (xylem) and non-lignifying (megagametophyte) tissue. Southern blot analysis of genomic DNA has also suggested the presence of a single Cad gene in spruce. Galliano *Plant Mol. biol.* 23:145 (1993). The CAD enzyme has been purified from loblolly pine xylem (O'Malley et al., *Plant Physiol.* 98:1364 (1992), and full-length pine Cad cDNA sequences have been isolated for two alleles of loblolly Cad (PtCadA, EMBL Data Library accession number Z37991; PtCadB, EMBL Data Library accession number Z37992) (MacKay et al., *Mol. Gen. Genet.* 247:537 (1995)). It has been speculated that the high level of naturally occurring variability of pine CAD enzyme is related to some of the variation in lignin and wood properties among individual pine trees. The maintenance of rare alleles, including nulls, is known to be favored in populations of gymnosperms. Allendorf et al. *Genetics* 100:497 (1982); Hamrick et al. *Amer. J. Botany* 76:1559 (1989). In contrast to these two gymnosperms, more than one Cad gene per haploid genome has been detected in tobacco (Knight et al. 1993), eucalypt (Grima-Pettenati et al. 1993), hybrid poplar and alfalfa (Van Doorsselaere et al., *Plant Physiol. Biochem.* 33:105 (1995). A CAD gene promoter sequence has also been isolated from tobacco (WO 93/24638 to M H Walter, assigned to Zeneca Ltd.).

The products of CAD have been postulated to have other functions in addition to their role in lignification, including involvement in the regulation of growth and differentiation. Binns et al., *Proc. Natl. Acad. Sci. USA* 84:980–984 (1987); Lynn et al. *Ann. Rev. Plant Physiol.* and *Plant Mol. Biol.* pp. 455–496 (1990). The activity of CAD in pine megagametophyte tissue suggests a role in embryo growth and development. MacKay et al., *Mol. Gen. Genetics* 247:537 (1995); O'Malley et al., *Plant Physiol.* 98:1364–1371 (1992). This role may be related to defense.

Few enzymes in phenylpropanoid metabolism have been characterized by loss of function/gain of function experiments in genetic tests. Alterations in the lignin biosynthetic pathway may affect total lignin content, lignin composition (proportions of aldehydes to alcohols or of different alcohols) or even lignin structure (type of intramolecular bonding). It has been suggested, based on CAD antisense tobacco plants, that CAD is not generally rate limiting for lignin synthesis. However, CAD may limit or control the proportion of coniferaldehyde subunits that are incorporated into the lignin polymer. The average lignin content of loblolly pine in different studies has ranged from 28.4% to 29.5% (Einspahr et al., *Forest Science* 10:165–173 (1964); (McMillin, *Wood Science and Tech.* 2:233–240 (1968) ; van Buijtenen et al., *Tappi* 44:141–144 (1961)).

In forest trees, null alleles exist for several enzymes, however, few of these have been characterized at the physiological or molecular level. The present inventors discovered a loblolly pine tree heterozygous for a null mutation for CAD. The null mutation segregated 1:1 in the haploid megagametophyte tissue of the seed. In megagametophytes and differentiating xylem carrying the null Cad gene, the level of CAD activity was 1% or less of the wild type. Steady state Cad message in such megagametophytes and xylem was also greatly reduced: between 1% and 3% of wild type, as detected using RNA gel hybridization and RT-PCR. In diploid embryos and xylem of 3 year old trees, the present inventors found that the null mutation was inherited as expected for a mutation linked to the Cad locus. Together these results suggested that the mutation was in the Cad gene and acted to reduce expression of the Cad gene. Sequence analyses of the null allele of Cad 7-56 clone indicated that the transcription unit and upstream flanking sequence (up to approximately 800 base pairs) are identical to a functional Cad allele of clone 7-56. Homozygous seed obtained from self-crosses of null heterozygotes germinated normally and the seedlings had brown-red xylem, indicative of altered lignin.

The present inventors have discovered a loblolly pine null mutation for CAD; this mutation results in the loss of function of CAD in lignifying tissue (xylem) as well as non-lignifying tissue (megagametophytes). The null mutation was discovered in the loblolly pine clone 7-56, which is an elite clone whose progeny have exceptional average growth and yield. Inheritance and mapping data indicated that the mutation is at or close to the Cad locus. This mutation is the first reported mutation in lignin biosynthesis in any tree (gymnosperm or angiosperm). It is one of the few characterized mutations in lignin in any plant. The present inventors have developed a method to breed populations of trees (particularly conifers, pine trees and loblolly pine trees) with reduced amounts of lignin, and/or with lignin of altered chemical composition.

A further aspect of the present invention is the identification of naturally occurring null variants of CAD genes from additional other loblolly pine clones, from other pine tree species, other gymnosperms and other plant species. After identification of CAD null variant genes and verification of the functional properties of CAD null genes, trees with useful genotypes resulting in reduced and/or chemically altered (i.e., more easily extractable) lignin can be propagated.

Additionally, the alteration in the lignin biosynthetic pathway which occurs in trees carrying the Cad null allele has been found by the present inventors to result in an increase in the amount of lignin pathway intermediates which are contained in the wood. Such intermediates include, but are not limited to vanillin, coniferaldehyde, and ferulic acid. Wood with increased intermediates may be valuable as a source of the intermediates; vanillin, for example, may be used to commercially produce vanilla flavoring. Vanillin extracted from wood has been used to produce vanilla flavoring, although petrochemical-based processes now predominate.

Null variant genes that encode enzymes occur in populations at low frequencies (approximately $3 \times 10^{-3}$ for pines). The spontaneous mutation rate for loss of gene function is approximately $10^{-5}$–$10^{-6}$. To identify null variants of CAD, large numbers of individual plants are screened for the absence of gene product (CAD), altered wood properties (e.g., reduced lignin content, lignin of altered chemical composition, brown-red coloration of xylem) and/or an altered Cad gene sequence. In pine and other conifers, CAD and other lignin biosynthetic enzymes are expressed in haploid megagametophyte tissue in seeds. In conifer species, the expression of a null CAD variant can easily be detected using megagametophyte tissue by the absence of gene products (mRNA or enzyme). It is easier to detect the absence of gene function in tissues containing only a single copy of the gene, and where the locus is not duplicated in the genome. In hardwoods, as opposed to conifers, the detection of null variants would require screening for quantitative differences in enzyme activity. In conifers containing only one Cad gene, two alleles of the gene will be present at the Cad locus in diploid tissues. Alleles of the Cad gene may be differentiated by native gel electrophoresis, and the inheritance of enzyme mobility variants can be readily analyzed using megagametophyte tissue from conifer seeds.

The plants to which the present invention can be applied include woody perennial plants and tree crops such as eucalyptus, poplar and pine species.

As used herein, "woody perennial plant" encompasses perennials such as trees, dwarf trees and shrubs. The method of the present invention may be applied to any tree, including both angiosperms and gymnosperms. Of the gymnosperms, conifers are particularly suitable for use in the present invention. Angiosperms suitable for use in practicing the present method include forest trees belonging to the genus Eucalyptus, Liquidambar (e.g, sweetgum), Liriodendron (e.g., yellow-poplar), Platanus (sycamore), Populus (e.g., cottonwoods, poplars, aspens) and domesticated trees such as those belonging to the genus Prunus (e.g., cherries and plums). Eucalyptus species are economically important in providing wood pulp to industries worldwide.

As used herein, the term "conifer" refers to a member of the order Coniferae in the sub-phylum Gymnospermae in the phylum Spermaphyta. Exemplary conifers which may be used in practicing the present invention are the members of the family Pinaceae, which include, for example, loblolly pine (*Pinus taeda*), slash pine (*Pinus elliotii*), longleaf pine (*Pinus palustris*), shortleaf pine (*Pinus echinata*), ponderosa pine (*Pinus ponderosa*), jack pine (*Pinus banksiana*), Eastern white pine (*Pinus strobus*), Western white pine (*Pinus monticola*), sugar pine (*Pinus lambertiana*), lodgepole pine (*Pinus contorta*), Monterey pine (*Pinus radiata*), Afghan pine (*Pinus eldarica*), Scots pine (*Pinus sylvestris*), and Virginia pine (*Pinus virginiana*); spruces such as the black spruce and the white spruce (genus Picea); Douglas fir (*Pseudotsuga menziesii*); hemlock species (such as *Tsuga canadensis*); spruce species (such as *Picea mariana, Picea rubens, Picea glauca* and Sitka spruce); redwood (*Sequoia sempervirens*); the true firs including silver fir (*Abies amabilis*), grand fir (*Abies grandis*), noble fir (*Abies procera*), white fir (*Abies concolor*), balsam fir (*Abies balsamea*); and the cedars which include Western red cedar (*Thuja plicata*), incense cedar (*Libocedrus decurrens*), Port Oxford cedar (*Chamaecyparis lawsoniona*), and Alaska yellow-cedar (*Chamaecyparis nootkatensis*); and Western larch (*Laryx occidentalis*). Preferred for practicing the present invention are the pines (genus Pinus) and the most preferred for practicing the present invention is the loblolly pine (*Pinus taeda*).

As used herein, "decreased" or "reduced" lignin in a plant refers to a reduction in the amount of lignin per unit dry weight compared to a wild-type plant of the same species. In a tree breeding program the reduction in lignin content per unit dry weight of wood, in a tree heterozygous for a Cad null allele, may be measured by comparison to a wild-type tree (i.e., one lacking a Cad null allele) of the same species, or to a parent tree lacking the Cad null allele. In a tree homozygous for a Cad null allele, the reduction in lignin content may be measured by comparison to a tree heterozygous for the Cad null allele (such as a parent tree), or to a wild-type tree of the same species. Lignin content may be measured using any of the methods which are known in the art.

As used herein, lignin which is more easily or more efficiently extractable refers to lignin whose composition renders it capable of more complete extraction using methods known in the art (i.e., the percentage of lignin which can be extracted from a unit of wood (dry weight) is increased), or capable of more efficient extraction using methods known in the art (i.e., reduced requirements for chemicals and/or energy), compared to wild-type trees of the same species. In a tree breeding program, in a tree heterozygous for a Cad null allele the alteration in lignin resulting in more easily or more efficiently extractable lignin may be measured by comparison to a wild-type tree (i.e., one lacking a Cad null allele) of the same species, or to a parent tree lacking the Cad null allele. In a tree homozygous for a Cad null allele, the alteration in lignin may be measured by comparison to a tree heterozygous for the Cad null allele (such as a parent tree), or to a wild-type tree of the same species. Ease or efficiency of lignin extraction may be assessed using any of the methods which are known in the art.

More easily extractable lignin can be indicated by any of the following: a greater percentage of thioglycolic acid extractable lignin (LTGA; see, e.g., Bruce and West, *Plant Physiol.* 91:889 (1989)); ability to extract a larger total percentage of the lignin from the wood using the same extraction method; or a reduced Kappa number (a measure of residual lignin known in the art) after standard lignin extraction processes. Each of the above noted characteristics is as compared to wild-type wood from same species.

As used herein, "increased" lignin intermediates in a plant refers to an increase in the compounds which are intermediates in the lignin biosynthetic pathway, including but not limited to coniferaldehyde, p-hydroxy benzaldehyde, ferulic acid, and p-coumaric acid. As used herein, "increased" degradation products refers to an increase in the compounds which are degradation products of lignin or lignin intermediates. Vanillin, for example, is a relatively stable degradation product of the unstable lignin intermediate coniferaldehyde. The increase may be measured per unit dry weight of wood, where an increase is assessed by comparison to a wild-type plant of the same species. In a tree breeding program, increases in compounds per unit dry weight of wood in a heterozygous Cad null tree may be measured by comparison to a wild-type tree (i.e., one lacking a Cad null allele) of the same species, or to a parent tree lacking the Cad null allele. In a tree homozygous for Cad null, the increase may be measured by comparison to a tree heterozygous for the Cad null allele (such as a parent tree), or to a wild-type tree of the same species. The amounts of lignin intermediates or degradation products may be measured using any of the methods which are known in the art.

The modified lignin biosynthetic pathway that is caused by the presence of one or two Cad null alleles, and which results in more easily extractable lignin, can be indicated by: brown-red xylem; unusually high levels of low molecular weight phenolics; lignin that is more accessible to degradation by mild alkali (e.g., 1N NaOH); increased amounts of vanillin, coniferaldehyde and/or ferulic acid (measured per unit dry weight of wood). Each of the above noted characteristics is as compared to wild-type wood from same species.

As used herein, a "Cad null allele" or "Cad null mutation" refers to a Cad gene that does not express active CAD enzyme. Any CAD activity due to a Cad null allele is lower than the minimum level detectable by methods used to assess CAD activity. As used herein, a "wild-type" Cad allele refers to an allele which expresses active CAD enzyme. A "wild-type" tree, as used herein, is a tree homozygous for wild-type Cad alleles; a heterozygote has one wild-type Cad and one Cad null allele.

As used herein, a "stand" of trees or plants refers to a plurality of individual plants growing in proximity to each other, such as in an agricultural field or a tree plantation, as is used in the art.

As used herein, a "stand of clonal trees" or plants refers to a stand of plants wherein multiple individuals within the stand are clones of each other, such that multiple trees within the stand have the same genome. A stand of clonal trees may consist of a plurality of trees, each having the same genome; or may consist of multiple individuals of several clones (i.e., each genome is represented by multiple individuals in the stand). In forestry it is a standard practice to mix several clones in a single stand as a safeguard; if one clone proves susceptible to a disease or otherwise performs unsatisfactorily, the other clones will be expected to perform differently. Thus, planting a plurality of clones of a single tree in a stand does not necessarily exclude the presence of additional clonal trees in that stand, with different genomes.

Trees may be grown in the field from seed. More commonly, seeds are germinated under controlled conditions and the seedlings are then planted in the field. As used herein, "planting" encompasses both planting seed directly at the agricultural site, as well as germinating seed in a greenhouse and planting the resulting seedlings at the agricultural site.

As used herein, "cloning" or "clonal propagation of plants" means asexually deriving one or more complete plants from a parent plant (or plant tissue), such that the derived plants are genetically identical to the parental plant or tissue.

The following examples are provided to illustrate the present invention, and should not be construed as limiting thereof. In these examples, nkat/gFW means nanokatals per gram of fresh weight of tissue (katals being a standard unit to assess enzyme activity).

EXAMPLE 1
Identification of Variants of CAD Enzyme in Loblolly Pine Seed

Enzyme staining methods were adapted using native PAGE to identify five electrophoretic mobility variants of CAD enzyme and to survey heterozygosity (O'Malley et al. *Plant Physiol.* 98:1364 (1992); MacKay et al., *Mol. Gen. Genetics* 247:537 (1995)). In pine, CAD is inherited as a single gene which is expressed both in xylem and in the haploid megagametophyte tissue (MacKay et al., *Mol. Gen. Genetics* 247:537 (1995)). The inheritance and segregation of CAD alleles can be demonstrated by detecting CAD enzyme variants in germinating pine seed tissues. Pine seeds contain haploid megagametophyte tissue, which is derived from the same meiospore that gives rise to the plant embryo. Therefore, each megagametophyte contains a single allele, the same as the maternally inherited allele of the embryo.

EXAMPLE 2
Single Gene Inheritance of Cad null Phenotype in Loblolly Pine Seed

Crude megagametophyte protein extracts were obtained from fifteen loblolly pine clone 7-56 seeds (open-pollinated) and separated by non-denaturing PAGE, and stained to reveal both CAD and glucose-6-phosphate dehydrogenase (G6PDH). FIG. 1. All seeds were found to be metabolically active as shown by the presence of G6PDH, but fewer than half (7) stained for CAD activity.

A 1:1 ratio for CAD activity was found in haploid megagametophyte tissue of loblolly pine clone 7-56 seeds, consistent with the Mendelian expectation for a single gene effect. CAD activity in megagametophyte tissue was further assessed in a total of 121 selfed clone 7-56 seeds, and a chi-squared statistical test for goodness of fit was carried out. Sixty-two of the seeds were active for CAD while 59 were null ($X^2$=0.074); all Mendelian ratios other than 1:1 were rejected.

A genetic map of loblolly pine clone 7-56 was generated using RAPD markers (see O'Malley et al., *Proceedings Staedler Symposium,* Columbia, Mo., May 23–26, (1995); Chaparro et al., *Theoretical Applied Genetics* 87:805 (1994); Roy et al., *TAG* 85:173 (1992)). Three RAPD markers were found to be closely linked (<11 centiMorgan) to the Cad locus in a loblolly pine tree unrelated to clone 7-56 (clone 6-1031) and having two wild-type Cad alleles. The markers linked to the Cad locus also co-segregated with the loss of CAD activity segregating in progeny of clone 7-56. The synteny of these three flanking markers suggested that the loss of function mutation maps to the Cad locus and is not due to a gross chromosomal rearrangement.

These results indicate that loblolly pine clone 7-56 is a heterozygote carrying a null mutation in a single gene—either the Cad gene or a closely linked gene that regulates CAD expression or function.

Figure 2A:
FIG. 2A is a native PAGE analysis of CAD null inheritance in seven progeny of loblolly pine clone 7-56, outcrossed with clone 11-118. 'M' indicates megagametophyte tissue and 'E' indicates embryo tissue extracts; extracts of the same seed were run side-by-side and stained for CAD activity. Diploid embryo tissue inheriting one Cad null allele (indicated by the absence of CAD activity in the corresponding megagametophyte tissue) gave a single band on PAGE for CAD activity stain; diploid tissue with two functional CAD alleles displays three bands because CAD is a dimeric enzyme.

EXAMPLE 3
Inheritance of Cad Null Allele in Heterozygous and Homozygous Diploid Tissues Loblolly pine clone 7-56 was crossed with loblolly pine clone 11-118 and seeds were collected. Clone 7-56 was produced as part of the North Carolina State University: Industry tree improvement program (Department of Forestry, PO Box 8002, North Carolina State University, Raleigh, N.C. 27695) and is available to and used by many commercial tree breeders. Megagametophyte (M) and embryo (E) extracts were obtained from each of seven seeds from the 7-56×11-118 cross. The tissue extracts from each seed were run side-by-side in native PAGE, and stained for CAD activity (MacKay, *Mol. Gen. Genetics* 247:537 (1995)). FIG. 2A shows inheritance of the CAD null allele in the seven seeds tested, where all embryo tissue stained for CAD, but megagametophyte tissue from only three of the seven seeds stained for CAD. Tree 11-118 has two alleles of CAD that differ in mobility on a native gel and both differ from the wild type allele of 7-56; 7-56 has a slow allele while 11-118 has one fast and one intermediate mobility allele. Outcrossed (7-56×11-118) seeds whose megagametophyte tissue showed no CAD activity were presumed to be heterozygous for Cad null (i.e., one Cad null allele and one wild-type Cad allele) in diploid tissue.

FIG. 2A is a native PAGE analysis of CAD null inheritance in seven progeny of loblolly pine clone 7-56, outcrossed with clone 11-118, where 'M' indicates megagametophyte tissue and 'E' indicates embryo tissue extracts. Extracts of the same seed were run side-by-side and stained for CAD activity. Diploid embryo tissue inheriting one Cad null allele (indicated by the absence of CAD activity in the corresponding megagametophyte tissue) gave a single band on PAGE for CAD activity stain; diploid tissue with two functional CAD alleles displays three bands because CAD is a dimeric enzyme. The single band of fast or intermediate mobility in diploid tissue heterozygous for Cad null suggests that the mutation results in a decrease in CAD expression rather than expression of a protein without catalytic activity. The fact that the Cad null allele remains inactive in diploid tissue indicates that the mutation is at the locus encoding CAD, rather than a mutation involving a trans acting regulatory function. The same pattern of allozyme inheritance was observed in xylem tissue of three year old trees, indicating that the mutation does not display tissue specificity.

Megagametophyte and embryo tissue extracts were also obtained from thirty selfed 7-56 germinated seeds, and stained for CAD and for shikimate dehydrogenase (SD) as a control. As shown in FIG. 2B and Table 1, several homozygous seed were germinated, indicating that the mutation was not lethal in homozygotes. FIG. 2B is a native PAGE analysis of CAD null inheritance in ten of the selfed progeny of loblolly pine clone 7-56; 'M' indicates megagametophyte tissue and 'E' indicates embryo tissue extracts. Extracts of the same seed were run side-by-side and stained for CAD activity and for shikimate dehydrogenase (SD) as a control. As shown in Table 1, one-third of the thirty total embryos had no enzyme activity (i.e., less than 1% of normal activity), slightly more than the expected 25%. A 1:3 ratio for presence vs. absence of CAD activity is consistent with the Mendelian expectation for a single gene effect segregating in diploid tissue. In more than half of the seeds tested, the megagametophyte tissue had no detectable CAD activity (i.e., less than 1% of normal activity) on native PAGE.

The above results indicate that the loblolly pine Cad null allele remains inactive in diploid homozygous tissue and that the Cad null allele is not lethal in homozygotes.

TABLE 1

Inheritance of Cad Null Enzyme Phenotype
in Selfed Seed Using Allozyme Gels

|  | Megagametophytes (Haploid) | Embryos (Diploid) |
| --- | --- | --- |
| Null | 19 | 10 |
| Wild Type | 11 | 20 |

EXAMPLE 4
Enzyme Activity and Steady State mRNA in Cad Null Megagametophytes, Shoot Tips and Xylem Tissue The expression levels of each CAD allele in loblolly pine 7-56 clone were studied using diploid xylem and haploid megagametophyte tissue. Enzyme activity was measured in xylem extracts using both the forward and reverse reactions of the enzyme (Campbell and Ellis, *Planta* 186:409–417 (1992); O'Malley et al., *Plant Physiol.* 98:1364 (1992)). Genotypes were determined using RAPD markers (see Example 2).

Figure 3B:
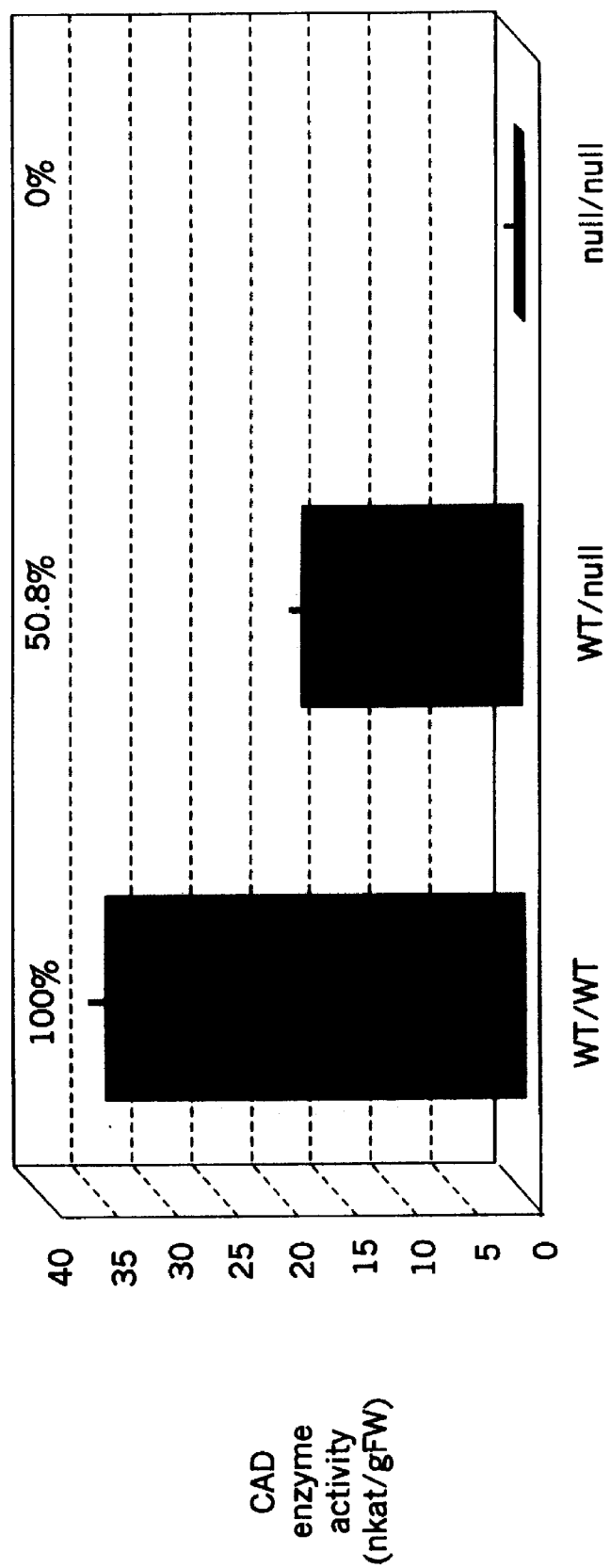
FIG. 3B is a graph comparing the CAD enzyme activity in xylem from homozygous wild-type (WT/WT), heterozygous Cad null (WT/null) and homozygous Cad null (null/null) loblolly pine trees. Enzyme activity in xylem of heterozygous Cad null plants was 50% of wild type, indicating that gene dosage and enzyme activity are highly correlated.

Enzyme activity was estimated by serial dilutions on native PAGE and in soluble assays using megagametophyte and xylem tissues. Megagametophytes had been scored as positive (+) or negative (−) for CAD activity on native PAGE. One percent or less of wild type CAD enzyme activity was found in the null megagametophytes and in xylem of null homozygotes (FIG. 3a). Homozygous null plants were found to have 1% on average of normal (wild type) activity. Enzyme activity in xylem of heterozygous Cad null plants (WT/null) was 50% of homozygous wild type (WT/WT), indicating that gene dosage and enzyme activity are highly correlated (FIG. 3b). CAD activity was measured in nanokatals per gram of fresh weight of tissue (nkat/gFW).

Northern blot analysis (probed with the Cad gene) using megagametophyte or whole shoot RNA from Cad null (NL) or wild-type (WT) loblolly pine plants, indicated the level of steady state message was lower than the threshold of detection (FIGS. 4A and 4B, top panels). The Northern blots were stripped and re-probed with a gene encoding a pine ribosomal protein as a positive control (FIGS. 4A and 4B, lower panels). RNAse protection assays with xylem RNA of wild-type (WT) or Cad null (NL) loblolly pine trees compared the steady-state RNA message of Cad compared to that of ribosomal protein and gave a similar result as the above Northern Blot analyses. The RNA transcript level in Cad null tissue was calculated to be less than 1–2% of wild type (FIG. 4C). As shown in FIG. 4C, each wild-type sample was run at 1 µg, 5 µg, and 20 µg of tissue; each null sample was run at 5 µg and 20 µg of tissue. The bottom panel of FIG. 4C is an over-exposure of the same film, giving the same comparative results.

These studies indicated that the Cad null allele and the corresponding loss of CAD enzyme activity correlates with a dramatic reduction in the level of steady state CAD mRNA.

EXAMPLE 5
Wood Phenotype in Selfed 7-56 Seedlings

Figure 5A:
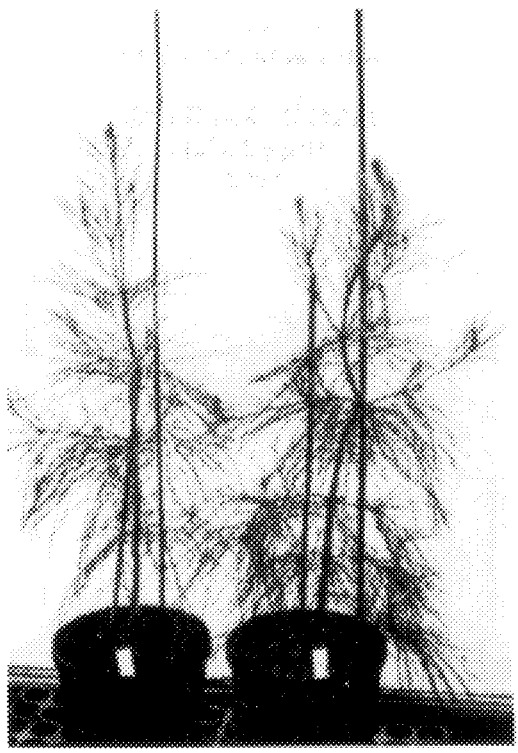
FIG. 5A shows 10-month old greenhouse seedlings, with a Cad null homozygous loblolly pine plant on the right, and wild-type loblolly pine on the left.
Figure 5B:
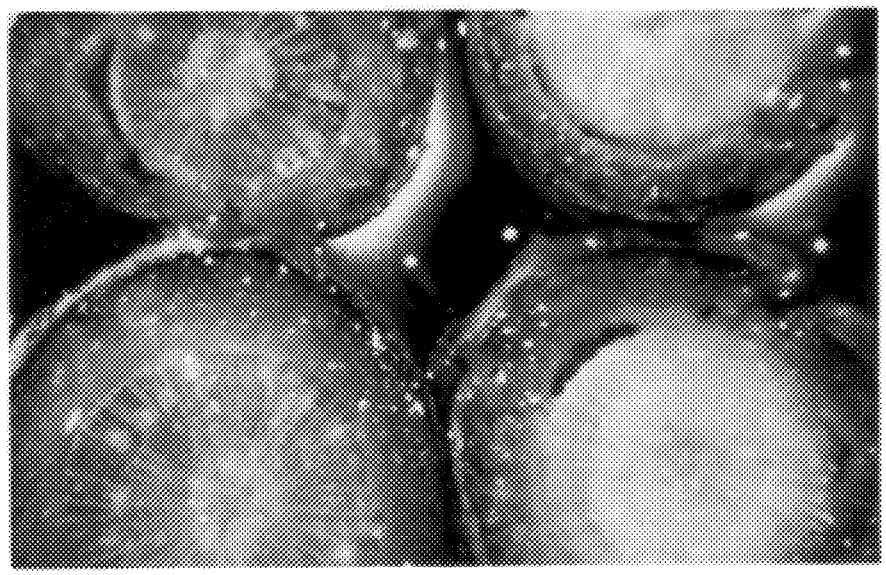
FIG. 5B depicts unstained sections of small branches cut from a Cad null homozygous loblolly pine (on the right) and a wild-type loblolly pine (on the left).
Figure 5C:
FIG. 5C depicts sections of small branches cut from a Cad null homozygous loblolly pine (on the right) and a wild-type loblolly pine (on the left) stained with phlorglucinol-HCl, which reacts with the aldehyde component of lignin.

Clone 7-56 was self-crossed to produce selfed seed and seeds were germinated. The progeny contained individuals with wild type wood (appearing white in cross section) and individuals with wood that appeared brown-red in cross sections (FIGS. 5B and 5C). The brown-red phenotype occurred at a frequency of approximately 0.25, as would be expected from a parent clone heterozygous for the Cad null mutation at a single gene.

Individuals with the brown-red wood phenotype were shown to be homozygous for the Cad null allele using RAPD marker analysis. Cad genotypes of individual clone 7-56 self-crosses were determined from RAPD markers tightly linked to the Cad null gene (collectively referred to as the 7-56 Cad null haplotype), as discussed above.

The RAPD analysis indicated that Cad null gene heterozygotes had a wild type (white) wood phenotype. Cad null gene homozygotes had a brown-red wood phenotype. In naturally occurring low CAD activity mutant maize and other grasses, a brown-red pigmentation in the xylem tissue is associated with mutations that modify lignin content and/or composition.

Staining of the brown-red wood from Cad null homozygotes, using phloroglucinol (Weisner stain) indicated a higher aldehyde content in the brown-red wood. The cellular morphology of wild-type and brown-red wood observed by light microscopy was indistinguishable.

EXAMPLE 6
Sequence of Cad Null Gene

Using DNA isolated from megagametophytes identified as containing either the Cad null allele or the wild-type allele, a nucleotide sequence was obtained for the 7-56 Cad null allele (SEQ ID NO:1). 800 base pairs of 5' upstream region have also been sequenced (sequence not shown); the sequences of the wild-type and Cad null haplotypes appear identical.

EXAMPLE 7
Infrared Absorbance Spectra of Wood in Selfed 7-56 Pine

Wood samples taken from plants with the white wood phenotype (normal) and with the brown-red wood phenotype discussed in the above example were examined using infrared absorption spectroscopy.

Figure 6A:
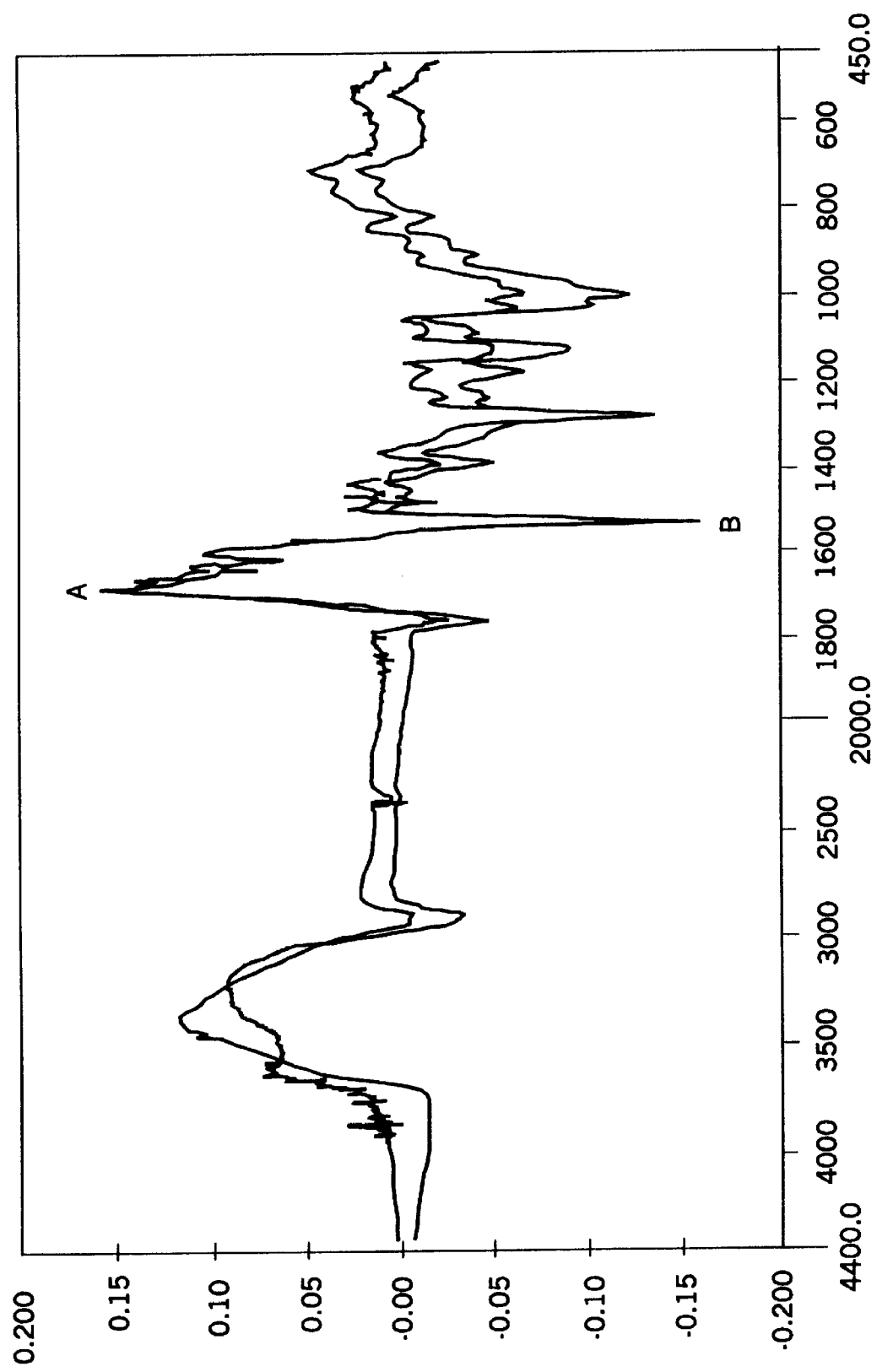
FIG. 6A graphs two infrared subtraction spectra, each obtained by subtracting the infrared spectra of a homozygous wild type loblolly pine tree from the infrared spectra of a homozygous Cad null loblolly pine. "A" indicates carbonyl groups conjugated to aromatic rings and is increased in the Cad null plants, compared to the wild-type plants; "B" indicates condensed and cross-linked lignin, and is reduced in the Cad null plants compared to the wild-type plants.

Fourier Transform Infrared Spectroscopy is a widely used method to investigate intact lignin in its native form in the wood, and contrasts with methods that involve the isolation of lignin and which rely on a chemical modification or degradation of the lignin polymer. The infrared spectra obtained using a homozygous wild type clone 7-56 loblolly pine tree was subtracted from that obtained using homozygous Cad null plants having a brown-red wood phenotype. FIG. 6A graphs two such spectra. "A" indicates carbonyl groups conjugated to aromatic rings (most likely due to coniferyl aldehyde). Each of the two subtraction spectra indicate that there is an increased amount of carbonyl groups conjugated to aromatic rings in the Cad null plants, compared to the wild-type plants. "B" indicates condensed and cross-linked lignin, and is reduced in the Cad null plants compared to the wild-type plants.

Figure 6B:
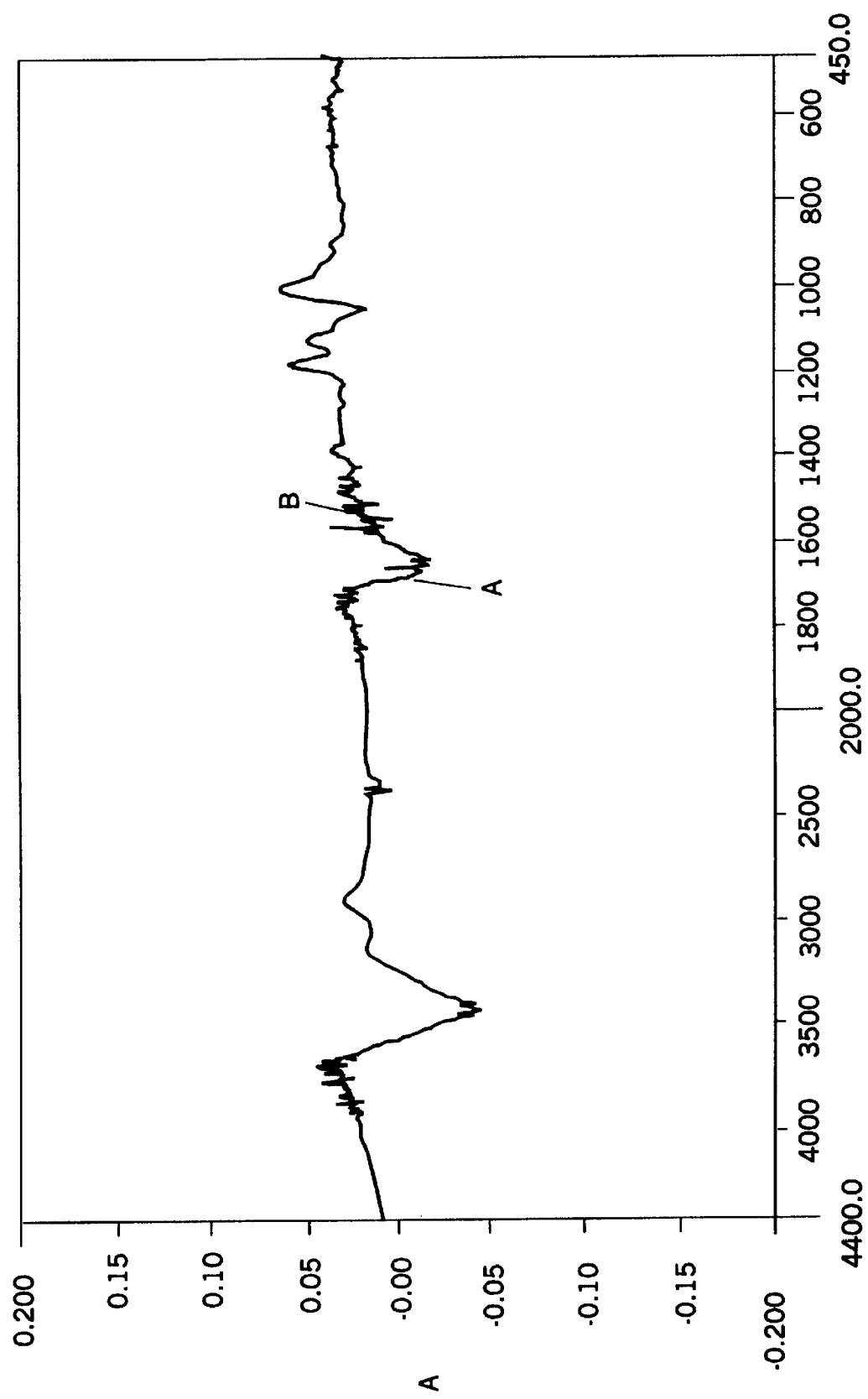
FIG. 6B graphs an infrared subtraction spectrum obtained by subtracting the spectrum of a homozygous Cad null loblolly pine from a second spectrum of a homozygous Cad null loblolly pine. "A" indicates carbonyl groups conjugated to aromatic rings, "B" indicates lignin.

FIG. 6B graphs the subtractive spectrum obtained by subtracting the spectra from two homozygous Cad null plants. "A" indicates carbonyl groups conjugated to aromatic rings, "B" indicates lignin.

FIG. 6C graphs the infra-red subtractive spectrum obtained by subtracting spectra from two wild-type loblolly pine plants (progeny of clone 7-56 with two functional Cad alleles). "A" indicates carbonyl groups conjugated to aromatic rings, "B" indicates lignin.

As show in FIGS. 6A–6C, wood samples taken from brown-red phenotype seedlings (homozygous Cad null) had a higher content of carbonyl groups conjugated to aromatic rings compared to that found in wild-type plants. Such chemical components could correspond to coniferyl aldehyde subunits which are expected to accumulate when CAD enzyme activity is blocked. The brown-red phenotype seedlings also absorbed less in the wavelength corresponding to the lignin backbone, indicating that their lignin content is also reduced or less condensed. The loss of CAD enzyme activity in null megagametophytes (shown in examples above), the brown-red wood coloration of homozygous null plants, and the changes in infra-red absorbance spectra establish that lignin is altered in loblolly pine seedlings homozygous for the Cad null gene, due to alterations in CAD enzyme activity.

Together the spectra in FIGS. 6B and 6C show that differences in the amount of aldehyde groups and the level of condensed or cross-linked lignin backbone only occur between the Cad null and wild type genotypes, and not within each one of these groups.

EXAMPLE 8

Lignin Characteristics in Homozygous Null Loblolly Pine

The Klason lignin method (see, e.g., Browning B L, *Methods of Wood Chemistry,* Institute of Paper Chemistry, Wis. (1967); Efflant, *Tappi J.* 60:143 (1977)) was used to determine lignin content in Cad null homozygotes and in wild-type loblolly pine. Lignin in wild type wood was 31.1±0.42% of the dry weight, whereas the Cad null homozygote had 28.1±0.31 (significantly different at the p=0.05 level). However, thioglycolic acid extractable lignin (LTGA; see, e.g., Bruce and West, *Plant Physiol.* 91:889 (1989)) was 50% more abundant in Cad null plants that the wild type, indicative of increased extractability. Table 2 shows that the amount of material recovered was 50% more with Cad null and that the absorbance ($A_{280}$) of the material was typical of lignin preparations and very similar in both genotypes.

TABLE 2

Lignin - TGA Analysis

|  | Weight (mg/g dry weight) ± s.d.* | $A_{280}$ (0.1 mg LTGA/ml) ± s.d.* | Total $A_{280}$/g dry weight ± s.d.* |
|---|---|---|---|
| Cad Null Wood | 229.1 ± 4.22 | 0.99 ± 0.035 | 2268 |
| Normal Wood | 156.5 ± 6.60 | 0.96 ± 0.047 | 1502 |

*s.d. = standard deviation

Extraction methods known in the art result primarily in the extraction from the wood of lignin monomers or pathway intermediates that are not bound, i.e., not incorporated into a lignin polymer. Lignin is not normally extracted using the solvents listed in Table 3. As used in Table 3, 'Total Phenolics' includes both lignin monomers and intermediates of the lignin pathway. As shown in Table 3, extractives recovered using known ethanol or methanol extraction techniques were two to three times more abundant in Cad null plants. The phenolic content of the extracts was measured as ferulic acid equivalents (using standard concentrations of ferulic acid as a reference) with the Folin Cialteau reagent (Booker et al., *New Phytol.* 132:483–490 (1996)). Alkaline hydrolysis of wood releases cell wall esterified phenolics and yielded 44 times more phenolics from the Cad null wood than from the wild type wood. These results indicate that the block in CAD caused by the Cad null allele results in accumulation of unusually high levels of low molecular weight phenolics. The lignin in Cad null wood may also be more extractable and more accessible to degradation by mild alkali (1N NaOH).

TABLE 3

Quantification of Free and Cell Wall Bound Phenolics

|  | Total Phenolics (mg Ferulate/g dry weight) | | |
|---|---|---|---|
|  | WT | Cad Null | Ratio Null/WT |
| Ethanol (50%) extraction | 3.3 ± 0.74 | 9.12 ± 1.04 | 2.75 |
| Methanol extraction (5 times) | 5.73 ± 0.96 | 11.31 ± 1.71 | 1.97 |
| NaOH (1N) Hydrolysis | 0.33 ± 0.18 | 14.67 ± 1.62 | 44.45 |

Figure 7:
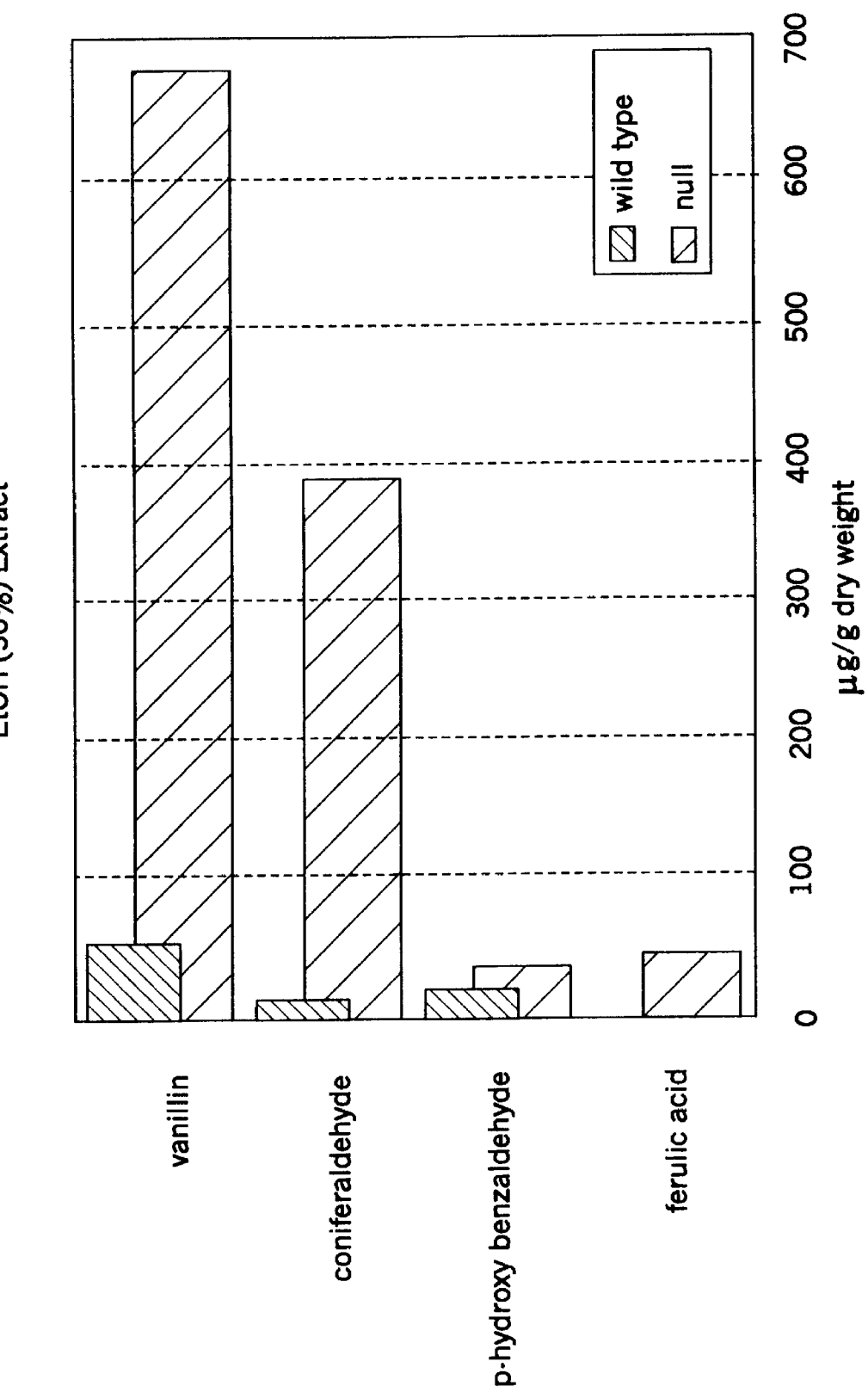
FIG. 7 graphs the phenolic extractives obtained using 50% ethanol in Cad null homozygous loblolly pine tissue (black bars), as compared to homozygous loblolly pine wild-type tissue (stippled bars).

The extracts obtained using 50% ethanol were acidified to pH 3.0 and analyzed by high performance liquid chromatography (HPLC), using standard methods known in the art (see Booker et al., *New Phytol.* 132:483 (1996). Co-elution with standard compounds was used for identification, and the relative amounts of lignin precursors were identified as shown in FIG. 7 (solid bars represent the Cad null homozygous wood; stippled bars represent homozygous wild type wood). Coniferaldehyde is a normal substrate of CAD, whereas vanillin is a degradation product from Coniferaldehyde. The amounts of vanillin, coniferaldehyde and ferulic acid (measured in µg/g dry weight) are increased in Cad null wood compared to wild type wood, indicating that the intermediates of the lignin pathway accumulate in Cad null wood. Most specifically the substrate of CAD accumulates to a high level, showing that (1) the mutation does not cause other major changes in the pathway; (2) coniferaldehyde is present and available for polymerization; and (3) the polymerization of coniferaldehyde is limited in some way.

Figure 8:
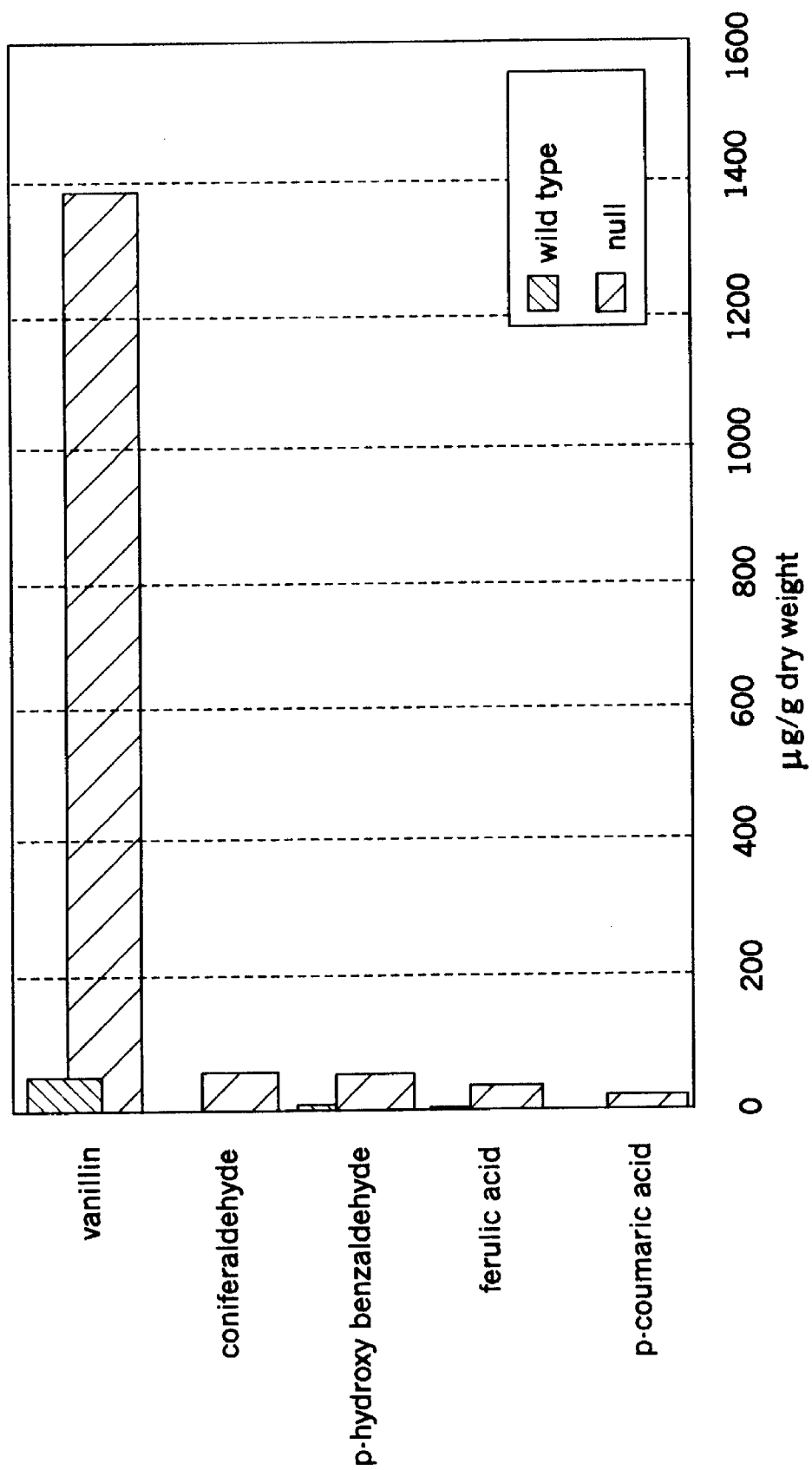
FIG. 8 is a graph showing the increased lignin biosynthetic pathway intermediates which are found in an NaOH (1 normal) extract of Cad null homozygous loblolly pine tissue (black bars), as compared to homozygous loblolly pine wild-type tissue (stippled bars).

As shown in FIG. 8, the extract obtained by NaOH hydrolysis was further analyzed by HPLC as described above to determine the relative amounts of lignin precursors or pathway intermediates (solid bars represent the Cad null homozygous wood; stippled bars represent homozygous wild type wood). The amounts of several components (measured in µg/g dry weight) are increased in Cad null wood compared to wild type wood. The most abundant compound is vanillin. The vanillin is most likely produced by oxidation of the coniferaldehyde released by the 1N NaOH.

The above result clearly shows that lignin precursor (most likely coniferaldehyde) is easily released from the wood fiber. This involves a weak bond such as an ester bond, not normally present in lignin. The coniferaldehyde that is released could be bound directly to the cell wall polysaccharide or be part of the lignin, in which case the above result further suggests that the modified lignin in the Cad null plants is more readily extracted.

EXAMPLE 9
Lignin Characteristics in a Nine-Year-Old Homozygous Null Loblolly Pine A nine-year-old homozygous null loblolly pine was produced by crossing two heterozygous Cad null offspring of clone 7-56. Wood from this tree is brown-red in color and was collected and measured using each of the chemical analyses discussed in Example 8, above; results were identical to the results provided in Example 8. As shown by the above Examples, homozygous Cad null trees contain decreased amounts of lignin and lignin of altered chemical composition, compared to wild-type trees.

Wood from this nine-year old tree is subjected to standard pulping methods to assess pulp characteristics. Micropulping techniques known in the art are used to compare the pulping characteristics of wood from the above described nine-year-old tree with a half-sib tree having a normal white wood phenotype. The yield, Kappa number (a measure of residual lignin known in the art), and bleachability of the pulp is assessed and compared.

EXAMPLE 10
Breeding and Selecting Cad Null Homozygotes

One use of Cad null genes is in breeding programs to deploy this gene in forest tree plantations to reduce lignin content or increase extractability in trees grown for the paper industry. Several different breeding strategies are used. However, in all cases, to obtain Cad null homozygotes two trees containing the Cad null gene first identified in loblolly pine clone 7-56 are crossed, which leads to potentially high levels of inbreeding. In most forest trees and specifically in pines, inbreeding results in decreased survival and slower growth. Two approaches are used to avoid such effects. First, individual trees that have adequate growth are selected in inbred populations and propagated vegetatively. Second, 7-56 and its offspring are recurrently outcrossed to unrelated trees, and offspring that inherit the null Cad allele are selected for use in further breeding. This approach provides trees with the Cad null allele, but having only 25% of the 7-56 genome after two generations of outcrossing, 12.5% after three generations, and 6.5% after four generations. Heterozygous offspring can be identified using RAPD markers as outline in Examples 3 and 4, above. Homozygous seedlings are easily identified by the brown-red color of the wood (e.g., a small branch can be removed without harming the plant). Crosses that are useful in generating homozygous Cad null progeny and the expected ratio of homozygous null:heterozygotes:homozygous wild type are as follows, ordered in decreasing level of inbreeding.

1) Selfing 7-56 (1:2:1) or Selfing a Cad null homozygote S1 progeny of 7-56 (1:0:0);
2) Backcrossing of an F1 (outcrossed) heterozygous progeny to 7-56 (1:2:1) or crossing a Cad null homozygote S1 to an F1 (outcrossed) heterozygous progeny to 7-56 (1:1);
3) Intercrossing two heterozygous F1 (outcrossed) progeny of 7-56 (1:2:1) or selfing any such F1 progeny (1:2:1);
4) Backcrossing of an F2 (recurrent outcrossed) heterozygous progeny to 7-56 (1:2:1) or crossing a Cad null homozygote S1 to a F2 (outcrossed) heterozygous progeny to 7-56 (1:1); and
5) Intercrossing two heterozygous F2 (recurrent outcrossed) progeny of 7-56 (1:2:1) or selfing any such F2 progeny (1:2:1).

Additional crosses that generate homozygous Cad null progeny and the expected ratio of homozygous null:heterozygotes:homozygous wild type, as well as the level of inbreeding, will be apparent to those skilled in the art.

The foregoing is illustrative of the present invention and is not to be construed as limiting thereof. The invention is defined by the following claims, with equivalents of the claims to be included therein.

That which is claimed is:

1. A method of producing a stand of conifer trees with each individual tree therein having easily extractable lignin, comprising the steps of:
    (a) identifying a sexually mature conifer tree homozygous for a Cad null allele;
    (b) crossing said conifer tree of (a) with a conifer tree of the same species to produce a plurality of seeds;
    (c) germinating a plurality of said seeds to produce a plurality of F1 progeny trees, each of said F1 progeny trees heterozygous or homozygous for the Cad null allele; and
    (d) growing a plurality of said F1 progeny trees in a stand; wherein each tree within said stand contains lignin which is more easily extractable compared to lignin in a wild-type tree of the same species.

2. The method of claim 1 wherein said conifer trees are a species of Pinus.

3. The method of claim 1 wherein said conifer trees are loblolly pine.

4. A stand of related trees having easily extractable lignin, said stand produced by the method of claim 1.

5. A method of producing a stand of clonal conifer trees having easily extractable lignin, comprising the steps of:
    (a) identifying a sexually mature conifer tree homozygous or heterozygous for a Cad null allele;
    (b) crossing said conifer tree of (a) with a conifer tree of the same species to produce a plurality of seeds;
    (c) germinating a plurality of said seeds to produce a plurality of F1 progeny trees;
    (d) assessing said progeny trees for the presence of said Cad null allele and selecting a single tree containing said Cad null allele;
    (e) cloning said single tree to produce a plurality of clonal trees; and
    (f) growing said plurality of clonal trees in a stand; wherein each tree within said stand contains lignin which is more easily extractable compared to lignin in a wild-type tree of the same species.

6. The method of claim 5 wherein said selected single tree is homozygous for said Cad null allele.

7. The method of claim 5 wherein said conifer trees are a species of Pinus.

8. The method of claim 5 wherein said conifer trees are loblolly pine.

9. A method of producing a stand of conifer trees having easily extractable lignin, comprising the steps of:
 (a) identifying a sexually mature conifer tree heterozygous for a Cad null allele;
 (b) crossing said conifer tree of (a) with a conifer tree of the same species and heterozygous for a Cad null allele to produce a plurality of seeds;
 (c) germinating a plurality of said seeds to produce a plurality of F1 progeny trees;
 (d) assessing said progeny trees for the presence of said Cad null allele and selecting those progeny trees which contain a Cad null allele; and
 (e) growing those progeny trees selected in step (d) in a stand;
wherein each tree within said stand contains lignin which is more easily extractable compared to lignin in a wild-type tree of the same species.

10. The method of claim 9 wherein said conifer trees are a species of Pinus.

11. The method of claim 9 wherein said conifer trees are loblolly pine.

12. A stand of clonal trees having easily extractable lignin, said stand produced by the method of claim 9.

13. A stand of conifer trees homozygous for a Cad null allele and containing lignin which is more easily extracted compared to wild-type trees of the same species.

14. A stand of conifer trees according to claim 13, wherein said stand comprises a plurality of trees which are clones of each other.

15. A stand of conifer trees according to claim 13, wherein said conifer trees are a species of Pinus.

16. A stand of conifer trees according to claim 13, wherein said conifer trees are loblolly pine.

17. A stand of clonal homozygous Cad null loblolly pine trees produced by the method of claim 5.

18. A stand of clonal homozygous Cad null loblolly pine trees.

19. A method of producing a stand of conifer trees with each individual tree therein having easily extractable lignin, comprising the steps of:
 (a) identifying a sexually mature conifer tree homozygous for a naturally occurring Cad null allele;
 (b) crossing said conifer tree of (a) with a conifer tree of the same species to produce a plurality of seeds;
 (c) germinating a plurality of said seeds to produce a plurality of F1 progeny trees, each of said F1 progeny trees heterozygous or homozygous for the Cad null allele; and
 (d) growing a plurality of said F1 progeny trees in a stand;
wherein each tree within said stand contains lignin which is more easily extractable compared to lignin in a wild-type tree of the same species.

\* \* \* \* \*